US010585065B2

(12) United States Patent
Kirk

(10) Patent No.: US 10,585,065 B2
(45) Date of Patent: Mar. 10, 2020

(54) PORTABLE EVIDENTIARY COLLECTION SYSTEM

(71) Applicant: Smiths Detection—Watford Ltd., Herts (GB)

(72) Inventor: Timothy C. Kirk, Gloucester, MA (US)

(73) Assignee: Smiths Detection-Watford Limited, Herfordshire (GB)

(*) Notice: Subject to any disclaimer, the term of this patent is extended or adjusted under 35 U.S.C. 154(b) by 708 days.

(21) Appl. No.: 14/434,505

(22) PCT Filed: Oct. 10, 2013

(86) PCT No.: PCT/US2013/064256
§ 371 (c)(1),
(2) Date: Apr. 9, 2015

(87) PCT Pub. No.: WO2014/059092
PCT Pub. Date: Apr. 17, 2014

(65) Prior Publication Data
US 2015/0268196 A1 Sep. 24, 2015

Related U.S. Application Data

(60) Provisional application No. 61/711,945, filed on Oct. 10, 2012.

(51) Int. Cl.
G01N 27/62 (2006.01)
H01J 49/00 (2006.01)

(52) U.S. Cl.
CPC ........ G01N 27/622 (2013.01); H01J 49/0036 (2013.01)

(58) Field of Classification Search
None
See application file for complete search history.

(56) References Cited

U.S. PATENT DOCUMENTS 7,381,972 B1 * 6/2008 Varmette ............. G01N 21/274
250/458.1
7,525,421 B2 4/2009 Levesque et al.
(Continued)

FOREIGN PATENT DOCUMENTS

EP 2144066 1/2010
JP 05-264505 10/1993
(Continued)

OTHER PUBLICATIONS

Ishida, Hiroshi et al., "Mobile robot navigation using vision and olfaction to search for a gas/odor source", Autonomous Robots, Kluwer Academic Publishers, BO, vol. 20, No. 3, Jun. 8, 2006, pp. 231-238.
(Continued)

Primary Examiner — Whitney Moore
(74) Attorney, Agent, or Firm — Kevin E. West; Advent, LLP

(57) ABSTRACT

Techniques are described for collecting information regarding the presence or absence of a material of interest in an environment and associating the presence or absence of the material of interest with additional data associated with the environment. In embodiments, the additional data is collected and associated with one or more windows identified for the materials of interest. A method includes initiating sample detection in an environment. The method also includes receiving an indication associated with at least one of a presence or an absence of a material of interest in the environment. The method also includes associating the indication with a time stamp furnished by a clock. The method further includes initiating collection of additional data associated with the environment. The additional data is associated with a second time stamp furnished by the clock.

(Continued)

The method also includes associating the indication with the additional data in a window.

19 Claims, 3 Drawing Sheets

(56) References Cited

U.S. PATENT DOCUMENTS

| | | | |
|---|---|---|---|
| 7,856,339 B2 | 12/2010 | Vock et al. | |
| 2003/0113922 A1 | 6/2003 | Cordery et al. | |
| 2007/0098391 A1* | 5/2007 | Howard | F21L 4/027 396/155 |
| 2007/0277589 A1 | 12/2007 | Harden et al. | |
| 2008/0118451 A1* | 1/2008 | Slibeck et al. | G08B 23/00 340/521 |
| 2008/0229805 A1 | 9/2008 | Barket et al. | |
| 2009/0189064 A1* | 7/2009 | Miller | G01N 27/624 250/282 |
| 2009/0261243 A1* | 10/2009 | Bamberger | H01J 49/0004 250/287 |
| 2010/0148946 A1* | 6/2010 | Strombeck | G08B 21/10 340/425.5 |
| 2010/0294925 A1* | 11/2010 | Musselman | H01J 49/10 250/282 |
| 2010/0332022 A1 | 12/2010 | Wegelin et al. | |
| 2011/0169646 A1* | 7/2011 | Raichman | G08B 21/245 340/573.1 |
| 2011/0253887 A1* | 10/2011 | Garfinkle | B65D 90/22 250/281 |
| 2012/0024272 A1 | 2/2012 | Iwazaki et al. | |
| 2012/0242472 A1 | 9/2012 | Walsh et al. | |

FOREIGN PATENT DOCUMENTS

| | | |
|---|---|---|
| JP | 2007534126 A | 11/2007 |
| JP | 2007537546 A | 12/2007 |
| WO | 2011077730 A1 | 6/2011 |
| WO | 2012054103 A1 | 4/2012 |

OTHER PUBLICATIONS

Extended European Search Report dated May 4, 2016 for EP Appln. No. 13845696.7.
Office Action dated Aug. 19, 2016 for MX Appln. No. 65769.
Office Action dated Jun. 20, 2017 for Japanese Applicaiton No. 2015-536879.
Search Report dated Sep. 29, 2017 for Russian Appln. No. 2015113228/28.
Office Action dated Sep. 29, 2016 for Chinese Appln. No. 201380060860.8.

* cited by examiner

PORTABLE EVIDENTIARY COLLECTION SYSTEM

BACKGROUND

Ion mobility spectrometry refers to an analytical technique that can be used to separate and identify ionized material, such as molecules and atoms. Ionized material can be identified in the gas phase based on mobility in a carrier buffer gas. Thus, an ion mobility spectrometer (IMS) can identify material from a sample of interest by ionizing the material and measuring the time it takes the resulting ions to reach a detector. An ion's time of flight is associated with its ion mobility, which relates to the mass and geometry of the material that was ionized. The output of an IMS detector can be visually represented as a spectrum of peak height versus drift time. In some instances, IMS detection is performed at an elevated temperature (e.g., above one hundred degrees Celsius (100° C.)). In other instances, IMS detection can be performed without heating. IMS detection can be used for military and security applications, e.g., to detect drugs, explosives, and so forth. IMS detection can also be used in laboratory analytical applications, and with complementary detection techniques such as mass spectrometry, liquid chromatography, and so forth.

SUMMARY

Techniques are described for collecting information regarding the presence or absence of a material of interest in an environment and associating the presence or absence of the material of interest with additional data associated with the environment. In embodiments, the additional data is collected and associated with one or more windows identified for the materials of interest. A method includes initiating sample detection in an environment. The method also includes receiving an indication associated with at least one of a presence or an absence of a material of interest in the environment. The method also includes associating the indication with a time stamp furnished by a clock. The method further includes initiating collection of additional data associated with the environment. The additional data is associated with a second time stamp furnished by the clock. The method also includes associating the indication with the additional data in a window.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

DETAILED DESCRIPTION

Figure 1:
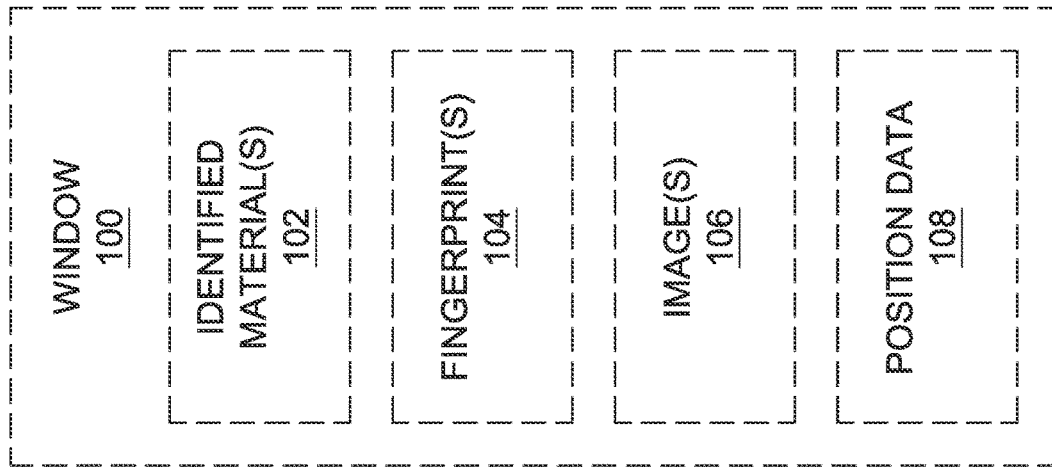
FIG. 1 is a diagrammatic illustration of information regarding the presence or absence of one or more materials of interest in an environment and additional data associated with the environment, where the additional data is collected and associated with one or more windows identified for the materials of interest in accordance with embodiments of the present disclosure.
Figure 1:
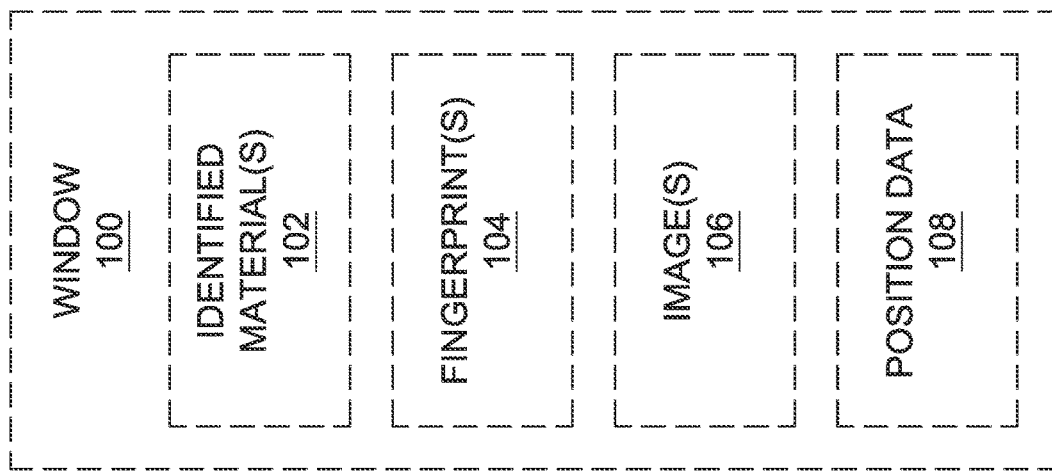
Figure 1:
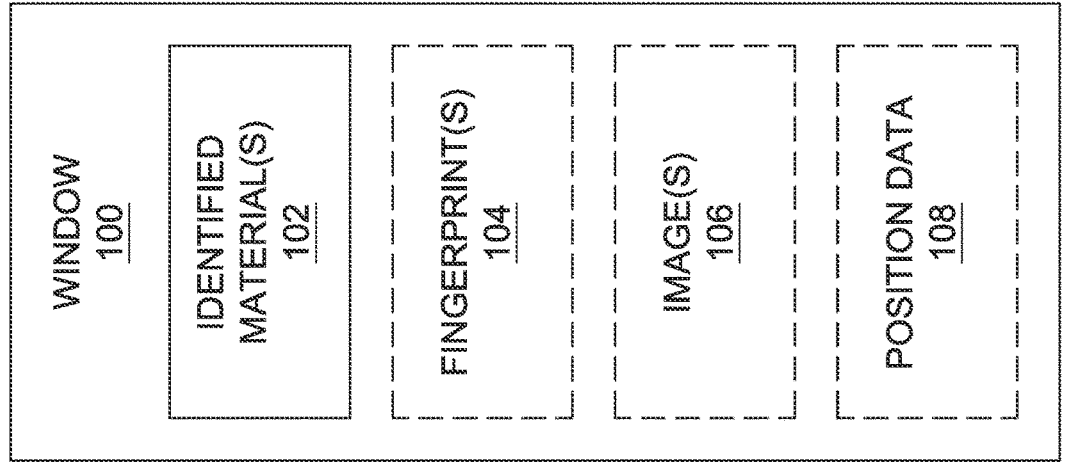
Figure 2:
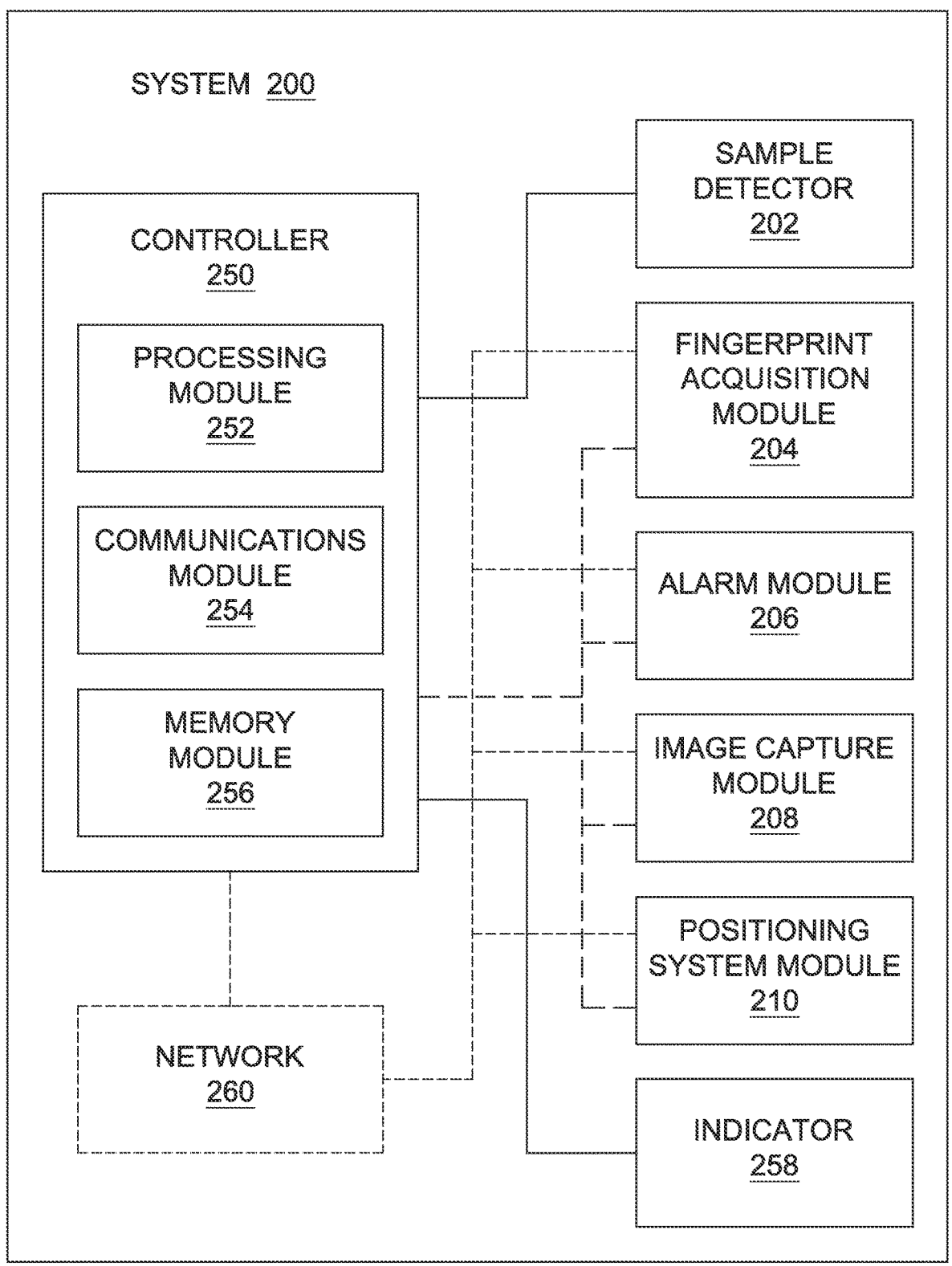
FIG. 2 is a diagrammatic illustration of a system including a controller operatively coupled with a sample detector, where the controller is also coupled with data collection equipment in accordance with embodiments of the present disclosure.
Figure 3:
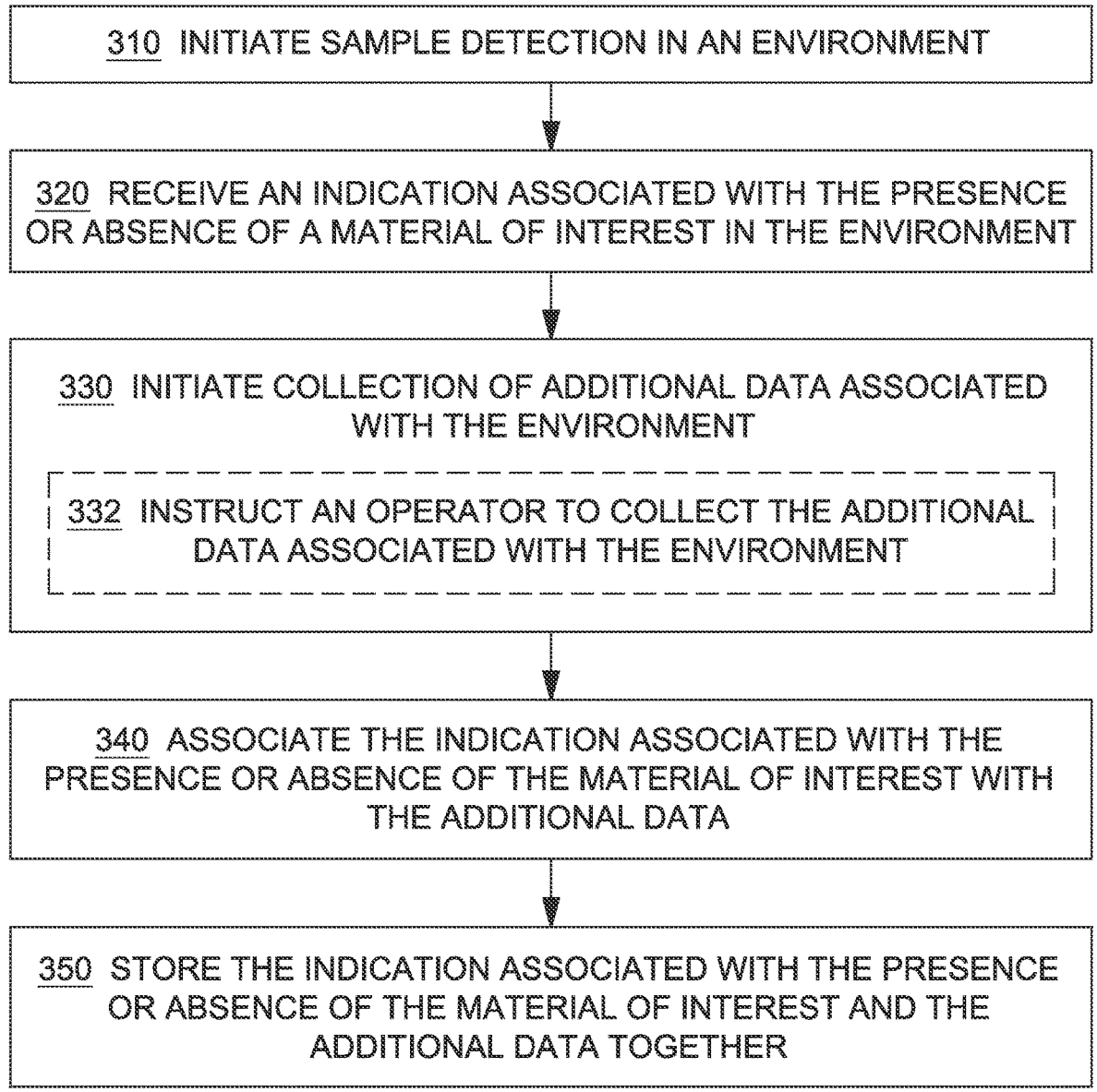
FIG. 3 is a flow diagram illustrating a method for collecting information regarding the presence or absence of a material of interest in an environment and associating the presence or absence of the material of interest with additional data associated with the environment in accordance with embodiments of the present disclosure.

Referring generally to FIGS. 1 through 3, systems and techniques are described for collecting information regarding the presence or absence of a material of interest in an environment and associating the presence or absence of the material of interest with additional data associated with the environment. In embodiments, the additional data is collected and associated with one or more windows identified for the materials of interest.

Sample detection is initiated in an environment (e.g., at a security checkpoint) (Block 310). The sample detection may be performed using an IMS system 200 as more fully detailed with reference to FIG. 2 below. Then, an indication associated with the presence or absence of a material of interest in the environment (e.g., identified material 102) is received (Block 320). For example, the IMS system 200 may detect an explosive substance. Next, collection of additional data associated with the environment is initiated (Block 330). For example, the IMS system 200 may initiate collection of fingerprints 104, images 106, position data 108, and so forth. In some embodiments, the IMS system 200 can provide an alert to instruct an operator to begin collection of the additional data (e.g., using an alarm module 206, an indicator 258, and so forth (Block 332).

Then, the indication associated with the presence or absence of the material of interest is associated with the additional data (Block 340). For example, fingerprints 104, images 106, position data 108, and possibly other data is associated with the identified materials 102. In embodiments of the disclosure, this information is associated using a characteristic time (e.g., a time stamp) generated using a common system clock, and possibly the position data 108. Then, the information including the indication associated with the presence or absence of the material of interest and the additional data is stored together in a logical structure comprising a window 100 (e.g., a folder within an electronic file directory structure) (Block 350).

In embodiments of the disclosure, the window 100 represents a collection of information associated with the received indication of the presence or absence of the material of interest. For example, the window 100 may be representative of a sequence of events based upon a clock, e.g., where the events are time stamped from a common system clock. In this context, the term "event" is used to refer to the collection of the indication of the identified materials 102, the fingerprints 104, the images 106, the position data 108 and so forth. Further, additional data can be stored in the window 100, including data representative of the status (e.g., health) of a sample detector 202. This additional data can also be time stamped.

In some embodiments, a system time stamp is used for the following events: sample complete, photo captured, position coordinates collected, and fingerprint scanned. In other embodiments, a system time stamp and position coordinates are collected and associated with the following events: sample complete, photo captured, and fingerprint scanned.

The system time stamp can be based upon a system time furnished by the controller 250, and this system time can be the master time for all events. The system time stamps can also be used to index and sort the events.

In some embodiments, the positioning system module 210 can be selectively activated and deactivated to conserve battery power. For example, the positioning system module 210 can be activated when an indication of a material of interest is received, and deactivated when the information associated with a window 100 has been collected. Further, in some instances, an indication of completion can be provided (e.g., to an operator and/or a remote monitoring authority). In embodiments, the window 100 is associated with a protocol representing desired information to be collected upon a triggering event, such as detection of a material of interest. Thus, completion of the protocol can be achieved when the desired information has been collected. Then, a new protocol can be initiated upon an additional triggering event. Further, different actions can be associated with different protocols. For example, detection of one material may initiate a protocol requiring a fingerprint, while detection of another material may initiate a protocol requiring a photograph but not a fingerprint.

It should also be noted that the requirements for a protocol can be dependent upon the information that is available to the IMS system 200. For example, positioning system time and coordinates may be required by a protocol when available (e.g., when the positioning system module 210 is active) and not required by the protocol when not available (e.g., when the positioning system module 210 is not active).

FIG. 2 is an illustration of a spectrometer system, such as an ion mobility spectrometer (IMS) system 200. Although IMS detection techniques are described herein, it should be noted that a variety of different spectrometers can benefit from the structures, techniques, and approaches of the present disclosure. It is the intention of this disclosure to encompass and include such changes. IMS systems 200 can include spectrometry equipment that employs unheated (e.g., surrounding (ambient or room) temperature) detection techniques. For example, an IMS system 200 can be configured as a lightweight explosive detector. However, it should be noted that an explosive detector is provided by way of example only and is not meant to be restrictive of the present disclosure. Thus, techniques of the present disclosure may be used with other spectrometry configurations. For example, an IMS system 200 can be configured as a chemical detector. An IMS system 200 can include a detector device, such as a sample detector 202 having a sample receiving port for introducing material from a sample of interest to an ionization region/chamber. For example, the sample detector 202 can have an inlet where air to be sampled is admitted to the sample detector 202. In some implementations, the sample detector 202 can have another device such as a gas chromatograph (not shown) connected in line with the IMS inlet.

The inlet can employ a variety of sample introduction approaches. In some instances, a flow of air can be used. In other instances, IMS systems 200 can use a variety of fluids and/or gases to draw material into the inlet. Approaches for drawing material through the inlet include the use of fans, pressurized gases, a vacuum created by a drift gas flowing through a drift region/chamber, and so forth. For example, the sample detector 202 can be connected to a sampling line, where air from the surrounding environment (e.g., room air) is drawn into the sampling line using a fan. IMS systems 200 can operate at substantially ambient pressure, although a stream of air or other fluid can be used to introduce sample material into an ionization region. In other instances, IMS systems 200 can operate at lower pressures (i.e., pressures less than ambient pressure). Further, IMS systems 200 can include other components to furnish introduction of material from a sample source. For example, a desorber, such as a heater, can be included with an IMS system 200 to cause at least a portion of a sample to vaporize (e.g., enter its gas phase) so the sample portion can be drawn into the inlet. For instance, a sample probe, a swab, a wipe, or the like, can be used to obtain a sample of interest from a surface. The sample probe can then be used to deliver the sample to the inlet of an IMS system 200. IMS systems 200 can also include a pre-concentrator to concentrate or cause a bolus of material to enter an ionization region.

A portion of a sample can be drawn through an inlet configured as a small aperture inlet (e.g., a pinhole) into the sample detector 202 using, for example, a diaphragm in fluid communication with an interior volume of the sample detector 202. For instance, when the internal pressure in the interior volume is reduced by movement of the diaphragm, a portion of the sample is transferred from the inlet into the sample detector 202 through the pinhole. After passing through the pinhole, the sample portion enters a detection module. The detection module can include an ionization region where the sample is ionized using an ionization source, such as a corona discharge ionizer (e.g., having a corona discharge point). However, a corona discharge ionizer is provided by way of example only and is not meant to be restrictive of the present disclosure. Other example ionization sources include, but are not necessarily limited to: radioactive and electrical ionization sources, such as a photoionization source, an electrospray source, a matrix assisted laser desorption ionization (MALDI) source, a nickel 63 source ($Ni^{63}$), and so forth. In some instances, the ionization source can ionize material from a sample of interest in multiple steps. For example, the ionization source can generate a corona that ionizes gases in the ionization region that are subsequently used to ionize the material of interest. Example gases include, but are not necessarily limited to: nitrogen, water vapor, gases included in air, and so forth.

In implementations, the detection module can operate in positive mode, negative mode, switch between positive and negative mode, and so forth. For example, in positive mode the ionization source can generate positive ions from a sample of interest, while in negative mode the ionization source can generate negative ions. Operation of the detection module in positive mode, negative mode, or switching between positive and negative mode can depend on implementation preferences, a predicted sample type (e.g., explosive, narcotic, toxic industrial chemicals), and so forth. Further, the ionization source can be pulsed periodically (e.g., based upon sample introduction, gate opening, the occurrence of an event, and so on).

The sample ions can then be directed toward a gating grid using an electric field. The gating grid can be opened momentarily to allow small clusters of sample ions to enter a drift region. For example, the detection module can include an electronic shutter or gate at the inlet end of a drift region. In implementations, the gate controls entrance of ions to the drift region. For example, the gate can include a mesh of wires to which an electrical potential difference is applied or removed. The drift region has electrodes (e.g., focusing rings) spaced along its length for applying an electric field to draw ions along the drift region and/or to direct the ions toward a detector disposed generally opposite the gate in the drift region. For example, the drift region, including the electrodes, can apply a substantially uniform field in the drift region. The sample ions can be collected at a collector electrode, which can be connected to analysis instrumentation for analyzing the flight times of the various sample ions. For instance, a collector plate at the far end of the drift region can collect ions that pass along the drift region.

The drift region can be used to separate ions admitted to the drift region based on the individual ions' ion mobility. Ion mobility is determined by the charge on an ion, an ion's mass, geometry, and so forth. In this manner, IMS systems 200 can separate ions based on time of flight. The drift region can have a substantially uniform electrical field that extends from the gate to a collector. The collector can be a collector plate (e.g., a Faraday plate) that detects ions based on their charge as they contact the collector plate. In implementations, a drift gas can be supplied through the drift region in a direction generally opposite the ions' path of travel to the collector plate. For example, the drift gas can flow from adjacent the collector plate toward the gate. Example drift gases include, but are not necessarily limited to: nitrogen, helium, air, air that is re-circulated (e.g., air that is cleaned and/or dried) and so forth. For example, a pump can be used to circulate air along the drift region against the direction of flow of ions. The air can be dried and cleaned using, for instance, a molecular sieve pack.

In implementations, the sample detector 202 can include a variety of components to promote identification of a material of interest. For example, the sample detector 202 can include one or more cells containing a calibrant and/or a dopant component. Calibrant can be used to calibrate the measurement of ion mobility. Dopant can be used to selectively ionize molecules. Dopant can also be combined with a sample material and ionized to form an ion that can be more effectively detected than an ion that corresponds to the sample material alone. Dopant can be provided to one or more of the inlet, the ionization region and/or the drift region. The sample detector 202 can be configured to provide dopant to different locations, possibly at different times during operation of the sample detector 202. The sample detector 202 can be configured to coordinate dopant delivery with operation of other components of an IMS system 200.

A controller 250 can detect the change in charge on the collector plate as ions reach it. Thus, the controller 250 can identify materials from their corresponding ions. In implementations, the controller 250 can also be used to control opening of the gate to produce a spectrum of time of flight of the different ions along the drift region. For example, the controller 250 can be used to control voltages applied to the gate. Operation of the gate can be controlled to occur periodically, upon the occurrence of an event, and so forth. For example, the controller 250 can adjust how long the gate is open and/or closed based upon the occurrence of an event (e.g., corona discharge), periodically, and so forth. Further, the controller 250 can switch the electrical potential applied to the gate based upon the mode of the ionization source (e.g., whether the detection module is in positive or negative mode). In some instances, the controller 250 can be configured to detect the presence of explosives and/or chemical agents and provide a warning or indication of such agents on an indicator 258.

In implementations, an IMS system 200, including some or all of its components, can operate under computer control. For example, a processor can be included with or in an IMS system 200 to control the components and functions of IMS systems 200 described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the IMS systems 200. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

The controller 250 may include a processing module 252, a communications module 254, and a memory module 256. The processing module 252 provides processing functionality for the controller 250 and may include any number of processors, micro-controllers, or other processing systems, and resident or external memory for storing data and other information accessed or generated by the controller 250. The processing module 252 may execute one or more software programs, which implement techniques described herein. The processing module 252 is not limited by the materials from which it is formed or the processing mechanisms employed therein, and as such, may be implemented via semiconductor(s) and/or transistors (e.g., using electronic integrated circuit (IC) components), and so forth. The communications module 254 is operatively configured to communicate with components of the sample detector 202. The communications module 254 is also communicatively coupled with the processing module 252 (e.g., for communicating inputs from the sample detector 202 to the processing module 252). The communications module 254 and/or the processing module 252 can also be configured to communicate with a variety of different networks 260, including but not necessarily limited to: the Internet, a cellular telephone network, a local area network (LAN), a wide area network (WAN), a wireless network, a public telephone network, an intranet, and so on.

The controller 250 is configured to communicate with a fingerprint acquisition module 204, an alarm module 206, an image capture module 208, and/or a positioning system module 210. The fingerprint acquisition module may be a fingerprint scanner. The alarm module 206 may furnish an audible alarm, a visual alarm (e.g., an indicator light), a tactile alarm, a signal transmitted to a remote monitoring authority, and so forth. The image capture module 206 may be a camera, a video camera, a thermal camera, an infrared camera, and so forth. The positioning system module 210 may comprise a receiver that is configured to receive signals from one or more position-transmitting sources. For example, the positioning system module 210 may be configured for use with a Global Navigation Satellite System (GNSS). The positioning system module 210 may also comprise a Global Positioning System (GPS) receiver operable to receive navigational signals from GPS satellites and to calculate a location as a function of the signals. The positioning system module 210 may also be configured for use with other position-determining systems including, but not limited to: a Global Orbiting Navigation Satellite System (GLONASS), a Galileo navigation system, other satellite or terrestrial navigation systems, and so forth. Further, the positioning system 210 may comprise an inertial navigation system (e.g., using one or more accelerometers, gyroscopes, and so forth). One or more of the fingerprint acquisition module 204, the alarm module 206, the image capture module 208, and/or the positioning system module 210 may be included with the sample detector 202 (e.g., in the same housing).

In some embodiments, the fingerprint acquisition module 204, the alarm module 206, the image capture module 208, and/or the positioning system module 210 can be directly coupled with the controller 250 (e.g., directly wired to the controller 250 using a wired network interface, such as an Ethernet connection, a data bus, and so forth). In other embodiments, the fingerprint acquisition module 204, the alarm module 206, the image capture module 208, and/or the positioning system module 210 can be wirelessly coupled with the controller 250 (e.g., via a secure Internet connection accessed using a wireless access point).

In embodiments of the disclosure, the controller 250 receives one or more electronic files representing fingerprints 104, images 106, and so forth (e.g., from the fingerprint acquisition module 204 and/or the image capture module 208) and associates (e.g., tags with metadata) each electronic file with a characteristic time (e.g., a time stamp) generated using, for instance, a common system clock. The controller 250 can store the electronic files together in a window 100 (e.g., a folder within an electronic file directory structure) using the memory module 256. The electronic files are stored in the window 100 with the data associated with the presence or absence of the identified materials 102. In some embodiments, position data 108, such as a characteristic position (e.g., one or more GPS locations determined using the positioning system module 210) can also be associated with and/or stored with the electronic files. In some embodiments, the controller 250 is configured to transmit the electronic files and the associated characteristic times and/or positions to a remote location (e.g., a remote monitoring authority) using, for example, the network 260.

The memory module 256 is an example of tangible computer-readable media that provides storage functionality to store various data associated with operation of the controller 250, such as software programs and/or code segments, or other data to instruct the processing module 252 and possibly other components of the controller 250 to perform the steps described herein. Thus, the memory can store data, such as a program of instructions for operating the IMS system 200 (including its components), spectral data, and so on. Although a single memory module 256 is shown, a wide variety of types and combinations of memory (e.g., tangible memory, non-transitory) may be employed. The memory module 256 may be integral with the processing module 252, may comprise stand-alone memory, or may be a combination of both.

The memory module 256 may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the sample detector 202 and/or memory module 256 may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

In implementations, a variety of analytical devices can make use of the structures, techniques, approaches, and so on described herein. Thus, although IMS systems 200 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A method, comprising:
   receiving a sample to be analyzed;
   ionizing the sample using an ionization source;
   directing the ionized sample towards a gating grid using an electric field;
   collecting ions of the ionized sample at a collector electrode;
   based at least in part of the collected ions, identifying one or more materials from their corresponding ions;
   comparing the identified one or more materials with one or more materials of interest;
   based at least in part on the comparison, receiving an indication of a presence or an absence of a material of interest;
   activating a positioning system to collect time and position coordinates information;
   associating the indication with a time stamp furnished by a common system clock;
   when the indication is associated with the presence of a material of interest, triggering selection of a protocol initiating collection of additional data, the additional data associated with a second time stamp furnished by the common system clock and a set of position coordinates, wherein the selection of the protocol is based at least in part on a type of the identified one or more materials of interest;
   associating the indication with the additional data in a window, wherein the window comprises data representing a sequence of events based on the common system clock, wherein the events comprise a collection of:
   (i) the indication; and
   (ii) the additional data;
   providing an indication of completion of the protocol when collection of additional data and the set of position coordinates is complete; and
   deactivating the positioning system when collection of additional data and the set of position coordinates is complete.

2. The method as recited in claim 1, wherein the receiving, ionizing, directing, collecting, identifying and comparing is performed using an ion mobility spectrometer (IMS) system.

3. The method as recited in claim 1, wherein the additional data comprises at least one of: a fingerprint, an image, or data representative of the status of a sample detector associated with the sample detection.

4. The method as recited in claim 1, further comprising initiating an alert to instruct an operator to begin collection of the additional data.

5. The method as recited in claim 1, wherein the window comprises a folder within an electronic file directory structure.

6. The method as recited in claim 1, wherein the window is associated with at least one other protocol specifying additional data to be collected in response to the indication being associated with the presence of a material of interest.

7. The method as recited in claim 6, wherein the specified additional data to be collected is determined based on the material of interest present in the environment.

8. The method as recited in claim 6, wherein the method comprises determining a form of the specified additional data based on forms of additional data available to the sample detector.

9. A system comprising:
a processor configured to:
receive a sample to be analyzed;
ionize the sample using an ionization source;
direct the ionized sample towards a gating grid using an electric field;
collect ions of the ionized sample at a collector electrode;
based at least in part of the collected ions, identify one or more materials from their corresponding ions;
compare the identified one or more materials with one or more materials of interest;
a sample detector communicatively coupled with the processor to provide the processor with an indication associated with at least one of a presence or an absence of a material of interest, based at least in part on the comparison;
a positioning system configured to collect time and position coordinates, the positioning system activated based at least on the indication associated with the presence of the material of interest; and
a memory configured to store the indication and additional data in a window, the additional data being collected when the indication is associated with the presence of a material of interest, the memory having computer executable instructions stored thereon, the computer executable instructions configured for execution by the processor to:
associate the indication with a time stamp furnished by a common system clock and a set of position coordinates;
trigger selection of a protocol initiating collection of the additional data, wherein the additional data is associated with a second time stamp furnished by the common system clock, wherein the selection of the protocol is based at least in part on a type of the identified one or more materials of interest, wherein the window comprises data representing a sequence of events based on the common system clock, wherein the events comprise a collection of:
(i) the indication; and
(ii) the additional data; and
deactivate the positioning system when collection of additional data and the set of position coordinates is complete.

10. The system as recited in claim 9, wherein the system comprises an ion mobility spectrometer (IMS) system.

11. The system as recited in claim 9, wherein the additional data comprises at least one of: a fingerprint, an image, or data representative of the status of the sample detector.

12. The system as recited in claim 9, further comprising an alarm operatively coupled with the processor, wherein the computer executable instructions are configured for execution by the processor to initiate an alert by the alarm to instruct an operator to begin collection of the additional data.

13. The system as recited in claim 9, wherein the window comprises a folder within an electronic file directory structure.

14. The system as recited in claim 9, wherein the additional data associated with the environment comprises position data, and wherein the position data is collected only when the indication is associated with the presence of the material of interest.

15. A method comprising:
receiving a sample to be analyzed;
analyzing the sample using a spectrometry system to identify one or more materials;
comparing the identified one or more materials with one or more materials of interest;
based at least in part on the comparison, receiving an indication associated with at least one of a presence or an absence of a material of interest;
activating a positioning system to collect time and position coordinates information;
associating the indication with a time stamp furnished by a common system clock;
triggering selection of a protocol initiating collection of additional data when the indication is associated with the presence of the material of interest, the additional data associated with a second time stamp furnished by the common system clock;
associating the indication with the additional data in a window, wherein the window comprises data representing a sequence of events based on the common system clock, wherein the events comprise a collection of:
(i) the indication; and
(ii) the additional data;
providing an indication of completion of the protocol when collection of additional data is complete; and
deactivating the positioning system when collection of additional data and the set of position coordinates is complete.

16. The method as recited in claim 15, wherein the receiving, analyzing and comparing are performed using an ion mobility spectrometer (IMS) system.

17. The method as recited in claim 15, wherein the additional data comprises at least one of a fingerprint, an image, position data, or data representative of the status of a sample detector associated with the sample detection.

18. The method as recited in claim 15, further comprising initiating an alert to instruct an operator to begin collection of the additional data.

19. The method as recited in claim 15, wherein the window comprises a folder within an electronic file directory structure.

* * * * *